(12) United States Patent
Nigg et al.

(10) Patent No.: US 6,562,845 B2
(45) Date of Patent: May 13, 2003

(54) MATERIALS AND METHODS FOR THE CONTROL OF TEPHRITIDAE FRUIT FLIES

(75) Inventors: Herbert N. Nigg, Lake Alfred, FL (US); Samuel E. Simpson, Lake Alfred, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/767,200

(22) Filed: Jan. 22, 2001

(65) Prior Publication Data

US 2001/0039288 A1 Nov. 8, 2001

Related U.S. Application Data

(63) Continuation of application No. 09/182,166, filed on Oct. 29, 1998, now abandoned.
(60) Provisional application No. 60/063,862, filed on Oct. 31, 1997.

(51) Int. Cl.$^7$ .......................... A01N 43/40; A01N 51/00; A01N 57/00; A01N 57/12; A01N 59/14
(52) U.S. Cl. .......................... 514/341; 514/64; 514/122; 514/143; 514/144; 424/657; 424/658; 424/659; 424/660
(58) Field of Search .......................... 514/341, 64, 122, 514/143, 144; 424/657, 658, 659, 660

(56) References Cited

U.S. PATENT DOCUMENTS 4,742,060 A * 5/1988 Shiokawa et al. .......... 514/252
5,720,968 A   2/1998 Shasha et al. .............. 424/410

FOREIGN PATENT DOCUMENTS

WO           930009        1/1993

OTHER PUBLICATIONS

Blickenstaff, "Common Names of Insects" Approved by The Entomo Logical Society of America, pp. 1 and 36 (1970).*
Overback, Brighton Crop Protection Con Ferance—Pests and Diseases (1990) pp. 21–28.*
Klotz, John H. and Byron L. Reid (1993) "Oral Toxicity of Chlordane, Hydramethylnon, and Imidacloprid to Free–Foraging Workers of *Camponotus pennsylvanicus* (Hymenoptera: Formicidae)" *J. Economic Entomology* 86(6):1730–1737.
Hu, P. et al. (1998) "Effects of sugar/flour spheres coated with paint and insecticide on alighting female *Ceratitis capitata* (Diptera: Tephritidae) flies" Biological Abstracts, vol. 1998, abstract No. 508934, also, Flordia Entomologist 81(3):318–325. Abstract only.
Van Steenwyk, R.A. et al. (1997) "Walnut husk fly control with low–toxicity insecticides", see abstract, also, Arthropod. Manage. (1988) Tests, 23:72. Abstract only.
Reissig, H. et al. (1992) "Apple, Secondary Insecticide Testing, 1991" *Insectic. Acaric. Tests* 17:39–40, see abstract.
Johnson, J.W. et al. (1992) "Apple, Broad–Spectrum Insect Control, 1992" *Insectic. Acaric, Tests* 18:49–50, see abstract.
Smith, R.F. et al. (1991) "Evaluation of Bay–NTN–33893 for Suppression of Apple Maggot Injury to Fruit" *Pestic, Res. Rep.*, p. 5, see abstract.
Polavarapu, S. et al. (1996) "Control of blueberry maggot on blueberries, 1995" *Arthropod. Manage. Tests* 21:62, see abstract.
Enkerin, W., J. Reyes, R. Villalobos (1993) "Use of Mixture of Boric Acid, Borax, Hydrolyzed Protein, and Water to Control *Anastrepha* Fruit Flies" In: Fruit Flies: Biology and Management, ed. Aluja, P. and Liedo, P., Springer–Verlag, NY, Inc., pp. 353–358.
F.D.Lopez, O. Hernandez Becerril (1967) "Sodium Borate Inhibits Decomposition of Two Protein Hydrolysates Attractive to the Mexican Fruit Fly" *J. Econ. Entomol.* 60(1):137–140.
F.D. Lopez, L.M. Spishakoff, O. Hernandez Becerril (1968) "Pelletized Lures for Trapping the Mexican Fruit Fly" *J. Econ. Entomol.* 61(1):316–317.
Newman, L.J. et al., Insect Pests Leaflets, Noll. Fruit Flies, Gov't Printer, Dept. of Agriculture, N.S.W. Australia, Leaflet No. 137. pp 1–6 (Date unavailable).
Kent, A.J. (1928) Insect Pests Leaflet No. 11—Fruit–Flies, Dept. of Agriculture, N.S.W., Australia. pp. 1–4.
Newman, L.J. et al. Fruit Fly (*Ceratitis capitata*). Baiting and Trapping Experiments, Leaflet No. 244, Gov't Printer, Dept of Agriculture, Western Australia. pp. 1–6 (Date unavailable).

* cited by examiner

Primary Examiner—John Pak
(74) Attorney, Agent, or Firm—Saliwanchik, Lloyd & Saliwanchik

(57) ABSTRACT

The subject invention provides materials and methods for the effective control of fruit flies. Specifically, the subject invention pertains to the use of imidacloprid compounds to control fruit flies. These compounds achieve a high level of control without mammalian toxicity.

4 Claims, 1 Drawing Sheet

MATERIALS AND METHODS FOR THE CONTROL OF TEPHRITIDAE FRUIT FLIES

CROSS REFERENCE TO RELATED APPLICATION

This application is a continuation of application Ser. No. 09/182,166, filed Oct. 29, 1998, now abandoned; which claims priority from provisional patent application U.S. Ser. No. 60/063,862, filed Oct. 31, 1997.

FIELD OF THE INVENTION

The present invention relates to compositions and methods to control fruit fly populations of the Tephritidae family.

BACKGROUND OF THE INVENTION

Fruit flies are a serious problem for the agriculture industry and cause extensive damage to, for example, citrus fruit. Extensive efforts have been made heretofore to exterminate these difficult and sometimes disease-bearing and/or fruit infecting insects.

A variety of methods have previously been utilized in efforts to control fruit flies. Unfortunately, these methods have significant drawbacks which limit their usefulness. For example, one common means for the control of fruit flies involves spraying malathion. Unfortunately, malathion, due to its toxicity, poses a serious threat to the environment and to human health.

Other methods of control have been attempted but without great success. For example, Enkerlin, W. et al. (Use of a Mixture of Boric Acid, Borax, Hydrolyzed Protein, and Water to Control Anastrepha Fruit Flies, Fruit Flies: Biology and Management, ed. Aluja, P. and Liedo, P., Springer-Verlag, NY, Inc., pp 353–358 [1993]) suggest that borate compounds may be used as insecticides against fruit flies and that a mixture of boric acid, borax, hydrolyzed protein and water may be used to control Anastrepha fruit flies.

Lopez, F. D. et al. (*J. Econ. Entomol.* 61(1):316–317 [1968]) disclose the use of pelletized lures formulated with borax and either PIB.7 (protein insect bait) or ENT-44, 014-X (enzyme hydrolyzed cottonseed protein) to trap and catch Mexican fruit flies.

Lopez, F. D. et al. (*J. Econ. Entomol* 60(1):137–140 [1967]) suggest that sodium borate inhibits decomposition of two protein hydrolysates attractive to the Mexican fruit fly.

Ken, A. J. et al. (Insect Pests Leaflets, Noll.-Fruit Flies, Gov't Printer, Dept. of Agriculture, N.S.W. Australia [1930]) disclose the use of lures containing borax to trap Mediterranean and Queensland fruit flies.

Newman, L. J. et al. (Fruit Fly (*Ceratitis capitata*); Baiting and Trapping Experiments, leaflet No. 244, Gov't Printer, Dept. Of Agriculture, Western Australia) disclose the use of arsenate of soda as a rapid killer of certain fruit flies and that trapping or luring methods utilizing arsenate of soda appear to be somewhat more effective than baiting methods.

Imidacloprid is an insecticidal compound known to have activity against sucking insects such as aphids, whiteflies, thrips, mealy bugs, leafhoppers, and scale insects. Use of imidacloprid to control fruit flies has not previously been disclosed or suggested.

There is a need in the art for improved toxicants that are effective against fruit flies of the family Tephritidae, that have attributes for direct and easy application, and that are not environmental pollutants or potential carcinogens.

BRIEF SUMMARY OF THE INVENTION

The present invention provides novel methods and compositions for controlling fruit flies of the family Tephritidae.

In a preferred embodiment, the present invention pertains to the use of imidacloprid compounds to control fruit flies. While the preferred toxicant contemplated by the present invention is imidacloprid (1-[(6-chloro-3-pyridinyl)methy]-N-nitro-2-imidazolidinime), other suitable compounds including derivatives, analogs, and salts of imidacloprid can be used as described herein.

Also, in accordance with the present invention, the imidacloprid toxicants may be utilized alone or in combination with baits, insecticides, other toxicants, agars, liquefiers, sweeteners, carriers and the like.

It should be appreciated by those of skill in this art that the fruit flies of the Trephritidae family, as contemplated by the present invention, include the Caribbean fruit flies, the Mediterranean fruit flies, the Mexican fruit flies, the Oriental fruit flies and any of the fruit flies which may be controlled by the methods and compositions of the present invention.

In accordance with the present invention, the methods and compositions are safe and effective and, therefore, can be used on any surface or at any location. In addition, the compositions of the present invention can be easily applied directly to areas of infestation and will remain active for extended periods of time. Therefore, the toxicants of the present invention may be used in residential preparations, commercial crop production, eradication programs and suppression programs for Tephritid fruit fly control.

The above features and advantages of the present invention will be better understood with reference to the detailed description and examples set out hereinafter. It will also be understood that the specific methods and compositions as set forth herein are exemplary only and are not to be regarded as limitations of this invention.

DETAILED DISCLOSURE OF THE INVENTION

Figure 1:
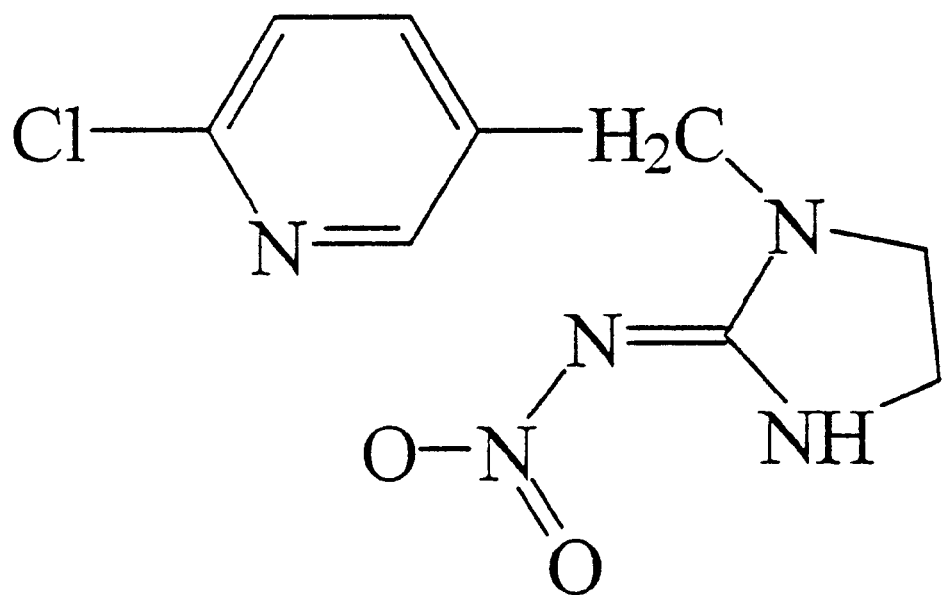
FIG. 1 shows the chemical structure of imidacloprid.

The subject invention pertains to materials and methods useful for the safe and effective control of fruit flies. In a preferred embodiment, the subject invention pertains to the control of fruit flies which attack citrus. In accordance with the subject invention, fruit flies are controlled by the application of an imidacloprid compound.

The imidacloprid compound used according to the subject invention may be imidacloprid itself or an analog, derivative, or salt which retains the advantageous fruit fly controlling properties of imidacloprid. The chemical structure of imidacloprid is shown in FIG. 1.

The fruit flies which can be controlled according to the subject invention include, but are not limited to, the Caribbean, Mediterranean, Mexican, and Oriental fruit flies.

The use of imidacloprid to control fruit flies as described herein is highly advantageous because imidacloprid is able to achieve a high level of control without toxicity to mammals, fish, or birds. The use of imidacloprid to control fruit flies has other important advantages including, for example, imidacloprid's low sensitivity to pH changes. This property of imidacloprid is advantageous because it expands the options for formulating and applying imidacloprid. In this regard, imidacloprid has been found to be compatible with a variety of baits.

Advantageously, it has been found that the use of imidacloprid compounds as described herein to control fruit flies results in a high toxicity to mature male and female fruit flies.

The subject invention includes the use of imidacloprid either alone as the active ingredient, or in combination with other compounds which can improve the efficacy or ease of the treatment. In accordance with the present invention, the compositions for use in controlling fruit flies include mixtures such as a mixture of an imidacloprid toxicant in an effective amount and, for example, a protein hydrolysate bait or any synthetic bait to generate a bait or lure in the form of a patty, heavy cream, pellet, gel, foam, paste, liquid or spray. The bait or lure may be in the free form or, alternatively, in a form, such as granules or tablets, agglomerated with or without the aid of a binder. Moreover, the bait or lure can be fixed or impregnated on a support or absorbed therein, and this support may include for instance, agar, paper, cardboard, plastic such as polystyrene, polyvinyl chloride, polyvinyl acetate and cellulose acetate, glass, pumice, crushed marble, silica or silica minerals. Optionally, other toxicants, such as Malathion, Dibrom® and Naled® can be used in conjunction with the imidacloprid application. Dibrom® and Naled® contain the insecticide 1,2-dibromo-2,2-dichloroethyl dimethyl phosphate.

Furthermore, attractants, such as Male Lure 11® and methyl eugenol, sweeteners, carriers and/or liquefiers may be used together with the imidacloprid compound. A bait or lure may be placed in selected locations such that the fruit flies are likely to encounter and ingest the toxicant to assure the desired effect, but preferably out of the way of normal human or animal traffic.

One embodiment of the present invention pertains to the use of an imidacloprid compound in wide-area suppression and eradication programs. Currently, toxic pesticides, such as malathion, are formulated with a protein hydrolysate bait, such as Miller's Nu-Lure®. According to the current invention, imidacloprid can be substituted for malathion in the formulation. In a specific embodiment, the protein hydrolysates are corn-based. The protein hydrolysate may be used full-strength or diluted to about 10% with water. The final proteinaceous bait spray may be used over wide areas.

A second innovative method for use in accordance with this invention is to formulate the toxicant with an extender or gel, such as Min-U-Gel®, Thixcin E®, Myverol® and CAB-O-SIL®. These are commercially available. In this case, gels can be sprayed in a solid stream to adhere to tree trunks, telephone poles, buildings and so forth. The gels are formulated with synthetic bait and/or natural proteinaceous baits. This method of application reduces worker and public inconvenience of aerial spraying of large areas. For the homeowner, either the gel formulation or the liquid formulation may be applied to individual host trees for Tephritid fly control.

It, of course, should be understood by those versed in this art that the compositions of the present invention may be applied by any suitable means, such as by pressurized applications, hydraulic oil squirt cans and aerial sprays.

The imidacloprid may be applied at a rate of, for example, about 0.1 ppm to about 100 ppm. More preferably, the imidacloprid compound is applied at a rate of about 1 ppm to about 25 ppm. Most preferably, the imidacloprid compound is applied at a rate of about 5 ppm to about 20 ppm. The application rate can be readily optimized for a particular use by a person skilled in the art having the benefit of the instant disclosure.

In one embodiment of the subject invention, imidacloprid can be used in conjunction with a borax toxicant for the control of fruit flies. When imidacloprid is used in conjunction with a borate compound, the preferred borate compound is borax (sodium borate decahydrate-10 mol $Na_2B_4O_7 \cdot 10H_2O$ or sodium borate pentahydrate-5 mol $Na_2B_4O_7 \cdot 5$. Other suitable borate compounds may be utilized in effective amounts as substitutes for borax or may be utilized in effective amounts in combination with borax or one another. Exemplary of borax-type compounds include anhydrous borax $Na_2B_4O_7$, ammonium tetraborate $(NH_4)_2B_4O_7 \cdot 4H_2O$, ammonium pentaborate $(NH_4)_2B_{10}O_{16} \cdot 8H_2O$, potassium pentaborate $K_2B_{10}O_{16} \cdot 8H_2O$, potassium tetraborate $K_2B_4O_7 \cdot 4H_2O$, sodium metaborate (8 mol) $Na_2B_2O_4 \cdot 8H_2O$, sodium metaborate (4 mol) $Na_2B_2O_4 \cdot 4H_2O$, disodium tetraborate decahydrate $Na_2B_4O_7 \cdot 10H_2O$, disodium tetraborate pentahydrate $Na_2B_4O_7 \cdot 5H_2O$ and disodium octaborate tetrahydrate $Na_2B_8O_{13} \cdot 4H_2O$. thus, the term "borax toxicant(s)" is used herein broadly and includes collectively and/or individually such borax and any other suitable borax type compounds. An effective molarity for a borax toxicant is in the range of between about 0.02 M and about 0.12 M or higher.

The mixtures, formulations and combination treatments of the subject invention can be readily carried out by one skilled in the art having the benefit of the instant disclosure.

In brief, the present invention overcomes and alleviates certain of the abovementioned drawbacks and shortcomings of the prior art and is directed to novel methods and compositions for killing or controlling fruit flies of the family Tephritidae.

It should be understood that the examples and embodiments described herein are for illustrative purposes only and that various modifications or changes in light thereof will be suggested to persons skilled in the art and are to be included within the spirit and purview of this application.

What is claimed is:

1. A method for controlling fruit flies of the family Tephritidae wherein said method comprises applying to said fruit flies an effective fruit fly controlling amount of imidacloprid or a salt thereof at a concentration from about 0.1 ppm to about 100 ppm in combination with an insecticide selected from the group consistion of malathion, a borate compound and 1,2-dibromo-2,2-dichloroethyl dimethyl phosphate.

2. The method, according to claim 1, wherein said imidacloprid or a salt thereof is imidacloprid.

3. The method, according to claim 1, wherein said fruit flies are selected from the group consisting of Caribbean fruit flies, Mediterranean fruit flies, Mexican fruit flies, and Oriental fruit flies.

4. The method, according to claim 1, wherein said imidacloprid is formulated with an extender to form a gel wherein said gel is applied to a surface which is likely to be contacted by said fruit flies.

* * * * *

UNITED STATES PATENT AND TRADEMARK OFFICE
CERTIFICATE OF CORRECTION

PATENT NO. : 6,562,845 B2
DATED : May 13, 2003
INVENTOR(S) : Herbert N. Nigg and Samuel E. Simpson It is certified that error appears in the above-identified patent and that said Letters Patent is hereby corrected as shown below:

<u>Column 4,</u>
Line 11, "$Na_2B_4O_710H_2O$" should read -- $Na_2B_4O_7 \cdot 10H_2O$ --.
Line 12, "$Na_2B_4O_7 \cdot 5Other$" should read -- $Na_2B_4O_7 \cdot 5H_2O)$ --.

Signed and Sealed this

Thirtieth Day of September, 2003

JAMES E. ROGAN
*Director of the United States Patent and Trademark Office*